United States Patent [19]

Roy

[11] Patent Number: 5,567,848
[45] Date of Patent: Oct. 22, 1996

[54] ALKYNE HYDROSILATION USING CYCLOALKADIENE-PLATINUM COMPLEX AS CATALYST

[75] Inventor: Aroop K. Roy, Midland, Mich.

[73] Assignee: Dow Corning Corporation, Midland, Mich.

[21] Appl. No.: 599,425

[22] Filed: Jan. 16, 1996

[51] Int. Cl.[6] .................................................. C07F 7/08
[52] U.S. Cl. ............................................................ 512/479
[58] Field of Search ............................................. 556/479

[56] References Cited

U.S. PATENT DOCUMENTS

| | | | |
|---|---|---|---|
| 2,823,218 | 2/1958 | Spieer et al. | 260/448.2 |
| 3,419,593 | 12/1968 | Willing | 260/448.2 |
| 4,292,434 | 9/1981 | Lindner et al. | 556/479 |
| 4,450,283 | 5/1984 | McAfee et al. | 556/479 |
| 4,898,961 | 2/1990 | Baile et al. | 556/479 |
| 5,142,037 | 8/1992 | Yamazaki et al. | 556/479 |
| 5,162,478 | 11/1992 | Barton et al. | 556/479 X |
| 5,270,424 | 12/1993 | Drake et al. | 556/479 X |

*Primary Examiner*—Paul F. Shaver
*Attorney, Agent, or Firm*—William F. Boley

[57] ABSTRACT

An improved process for hydrosilating alkynes with hydridosilane using a cycloalkadiene-platinum complex as catalyst. The use of the cycloalkadiene-platinum complex as catalyst in the process reduces formation of the bis-silated adduct of the alkynes, when compared to the use of standard platinum-based hydrosilation catalysts.

20 Claims, No Drawings

ALKYNE HYDROSILATION USING CYCLOALKADIENE-PLATINUM COMPLEX AS CATALYST

BACKGROUND OF INVENTION

The present invention is an improved process for hydrosilating alkynes with hydridosilanes using a cycloalkadiene-platinum complex as catalyst. The use of the cycloalkadiene-platinum complex as catalyst in the process reduces formation of the bis-silated adduct of the alkynes, when compared to the use of standard platinum-based hydrosilation catalysts.

Virtually any compound which contains a $\equiv$SiH group can be reacted with compounds containing aliphatic unsaturation in the presence of a platinum compound such as chloroplatinic acid to effect a reaction typically referred to as hydrosilation or hydrosilylation. Speier et al., U.S. Pat. No. 2,823,218, discuss such hydrosilation reactions in detail.

Willing, U.S. Pat. No. 3,419,593, describes a group of catalysts that are the reaction product of chloroplatinic acid with organosilicon compounds having terminal unsaturation that are particularly useful in many such hydrosilation processes.

Lindner et al., U.S. Pat. No. 4,292,434, describe a hydrosilation catalyst obtained by dissolving a platinum halide in at least 20 parts by weight of an olefin, such as 1,5-cyclooctadiene, for each part by weight of platinum halide and subsequently heating and mixing the solution obtained with from 0.5 to one mole of a primary or secondary amine for each gram atom of platinum. The catalyst is described as useful in the reaction of acetylene with methyldichlorosilane to produce vinylmethyldichlorosilane. However, the present inventor has discovered that at the 1,5 cycloalkadiene to platinum molar ratio described by Lindner et al. (approximately 80:1) the 1,5 cyclooctadiene acts as an inhibitor of the reaction.

A common problem associated with the hydrosilation of an alkyne with a hydridosilane in the presence of a platinum halide or platinum olefin complex as catalyst is the formation of the bis-silated adduct of the alkyne as a by-product. Typically such hydrosilation processes are run under high pressure to increase the concentration of alkyne in the reaction mixture relative to the alkenyl substituted product thereby minimizing the formation of the bis-silated adduct. However alkynes such as acetylene are explosive at high pressures, thereby making such processes dangerous. The present inventor has discovered that in processes where an alkyne is silated with a hydridosilane in the presence of a cycloalkadiene-platinum complex as catalyst the amount of the bis-silated adduct formed is reduced, when compared to standard platinum-based hydrosilation catalysts. This can allow such processes to be run at near normal atmospheric pressure while still providing for an acceptable ratio of alkenyl substituted product to bis-silated adduct by-product.

SUMMARY OF INVENTION

The present invention is an improved process for hydrosilating alkynes with hydridosilane using a cycloalkadiene-platinum complex as catalyst. The use of the cycloalkadiene-platinum complex as catalyst in the process reduces formation of the bis-silated adduct of the alkynes, when compared to the use of standard platinum-based hydrosilation catalysts.

DESCRIPTION OF INVENTION

The present invention is a process for hydrosilation of an alkyne. The process comprises: contacting at a temperature within a range of about 40° C. to 150° C. an alkyne described by formula

$$R^1C\equiv CH, \quad (1)$$

where $R^1$ is selected from a group consisting of hydrogen atom and alkyls comprising one to about ten carbon atoms; with a hydridosilane described by formula

$$(R^2)_nHSiX_{3-n}, \quad (2)$$

where each $R^2$ is independently selected from a group consisting of alkyls comprising one to about 20 carbon atoms and aryls, each X is an independently selected halogen, and n=0 to 3; in the presence of a platinum catalyst consisting essentially of a cycloalkadiene-platinum complex described by formula $PtR^3{}_2$ or $Pt(R^3)X_2$, where $R^3$ is a cycloalkadiene comprising about six to 20 carbon atoms and X is as previously described.

The alkyne can be contacted with the hydridosilane in standard low-pressure type reactors suitable for reacting such compounds. The pressure at which the present process is conducted is not critical and can be varied within a wide range. However, the present process is advantageous in that it can be conducted at near-normal atmospheric pressure while still providing for an acceptable ratio of alkenyl-substituted product to bis-silated by-product. Therefore, it is preferred that the process be conducted at a pressure within a range of about 0.1 to 3 atmospheres. More preferred is when the process is conducted at a pressure within a range of about 1 to 3 atmospheres.

The present process can be conducted in either a gas or liquid phase. However, it is preferred that the process be conducted in a liquid phase using a liquid hydrocarbon solvent in which the alkyne and hydridosilane are soluble. It is preferred that the liquid hydrocarbon solvent have a boiling point greater than the boiling point of the alkenyl substituted product of the process to facilitate separation of the product from the solvent. The solvent can be, for example, an aromatic hydrocarbon such as xylene or a mixture of the isomers of xylene, toluene, or benzene. An example of such a liquid phase process is provided in the Examples herein.

The present process is conducted at a temperature within a range of about 40° C. to 150° C. A preferred temperature is within a range of about 60° C. to 100° C. The optimal temperature for conducting the process will depend upon such factors as the alkyne and hydridosilane to be reacted. For example, when acetylene is reacted with methyldichlorosilane a preferred temperature for conducting the process is within a range of about 70° C. to 80° C. and when acetylene is reacted with dimethylchlorosilane a preferred temperature is within a range of about 60° C. to 70° C.

Alkynes useful in the present process are described by formula (1), where $R^1$ is selected from a group consisting of hydrogen atoms and alkyls comprising one to ten carbon atoms. $R^1$ can be, for example, methyl, ethyl, propyl, tert-butyl, and decyl. Preferred is when $R^1$ is hydrogen, making the alkyne acetylene.

Hydridosilanes useful in the present process are described by formula (2), where $R^2$ is selected from a group consisting of alkyls comprising one to 20 carbon atoms and aryls, each X is an independently selected halogen, and n has a value of zero, one, two, or three. $R^2$ can be, for example, alkyls such as methyl, ethyl, propyl, and tert-butyl; halogen substituted alkyls such as chloromethyl and 3,3,3-trifluoropropyl; aryls such as phenyl, tolyl, and xylyl; and halogen substituted aryls such as chlorophenyl. Preferred is when $R^2$ is methyl. Preferred is when X is a chlorine atom. The preferred hydridosilane is selected from a group consisting of methyldichlorosilane and dimethylchlorosilane.

In the present process it is preferred that the mole ratio of the alkyne to the hydridosilane fed to the process be within a range of about 0.5:1 to 3:1. Preferred is when the mole ratio of alkyne to hydridosilane is within a range of about 1:1 to 1.3:1.

The present process is conducted in the presence of a platinum catalyst consisting essentially of a cycloalkadiene-platinum complex described by formula $PtR^3{}_2$ or $Pt(R^3)X_2$, where $R^3$ is a cycloalkadiene comprising about six to 20 carbon atoms and each X can be an independently selected halogen atom. Preferred is when the cycloalkadiene comprises about 6 to 10 carbon atoms. The cycloalkadiene can be a, for example, cyclohexadiene, cycloheptadiene, cyclooctadiene, cyclodecadiene, and norbornadiene. The preferred cycloalkadiene is 1,5-cyclooctadiene. Preferred is when X is chlorine atoms. The most preferred platinum catalyst is described by formula $Pt(R^3)Cl_2$, where $R^3$ is 1,5-cyclooctadiene. Procedures for making platinum catalysts useful in the present process are found, for example, in Drew et al., Inorg. Synth. 28:346–349 (1990) and in Crascall et al., Inorg. Synth. 28:126–132 (1990).

The concentration of platinum catalyst used in the present process can be varied within wide limits. In general, when the process is run as a batch process in the liquid phase the catalyst concentration in the liquid phase can be that providing about one to 20,000 ppm platinum. Preferred is when the catalyst provides about 20 to 10,000 ppm platinum in the liquid phase.

The present process can further comprise the presence of non-complexed cycloalkadiene comprising about six to 20 carbon atoms with the proviso that the ratio of total moles of cycloalkadiene per g-atom of platinum be less than about five. Where, the "total moles of cycloalkadiene" is that provided to the process by the cycloalkadiene-platinum complex plus any additional non-complexed cycloalkadiene present in the process. The additional non-complexed cycloalkadiene may be added to the process separate from the cycloalkadiene-platinum complex or may be provided to the process as a mixture with the cycloalkadiene-platinum complex. Preferred is when the ratio of total moles of cycloalkadiene to g-atom of platinum is less than about 3. Even more preferred is when the ratio of total moles of cycloalkadiene to g-atom of platinum is less than about 2.5. When present, it is preferred that the non-complexed cycloalkadiene be the same as that complexed with the platinum to form the cycloalkadiene-platinum complex.

The following examples are provided to illustrate the present invention. These examples are not intended to limit the scope of the claims herein.

The apparatus set-up for running the examples is as follows. Commercially acquired acetylene was purified to remove stabilizing agents. The purified acetylene was introduced via a coarse glass-frit gas dispersion tube into a 500 mL, 3-neck, round-bottom flask containing liquid hydridosilane. This flask, termed the "SiH reservoir", was fitted with a thermometer and equipped with teflon adapters at the necks for entry of delivery and exit tubes. The exit tube from the SiH reservoir was a 6 mm O.D. polypropylene tube leading to a 500 mL flask used as a safety trap between the SiH reservoir and the reaction flask. The tubing exiting the safety trap was a 3 mm O.D. teflon tube. This exit tube was connected to a second gas dispersion tube which entered a 1 L, 3-neck, round-bottom flask termed the "reactor". The reactor was equipped with a stirring bar and fitted with a thermometer at one neck and a claisen adapter on the center neck. The straight neck of the claisen adaptor was equipped with a rubber septum for the periodic withdrawal of samples from the reactor for analysis by gas chromatography using a thermal conductivity detector (GC-TCD). The second neck of the claisen adapter was fitted with a dewar condenser cooled with a dry ice/isopropyl alcohol (IPA) bath. The tygon tubing exiting this condenser led to a mineral oil double-bubbler via a dry ice/IPA trap. Provisions were made for blanketing and or purging the apparatus with nitrogen gas from just before the SiH reservoir to between the last dry ice/IPA trap and the bubbler.

The experimental procedure for running the examples was as follows. Methyldichlorosilane or dimethylchlorosilane was added to the SiH reservoir, which was maintained at a constant temperature of about 18° C. when the hydridosilane was methyldichlorosilane and about 13° C. when the hydridosilane was dimethylchlorosilane. A preweighed quantity of catalyst and where indicated 1,5-cyclooctadiene (COD) was added to the reactor. Based on approximately one g-mol of product formed during a run, the amount of catalyst used provided a final Pt/SiH g-atom to mole ratio of about $6\times 10^{-5}:1$ in each example. Methylvinyldichlorosilane or dimethylvinylchlorosilane (as a means of varying the average vinylsilane concentration in the reactor) and xylenes in the amounts described in each example were transferred to the reactor under a slow nitrogen purge.

The reaction apparatus was purged with acetylene and then the gas dispersion tube in the SiH reservoir was slowly lowered into the hydridosilane so as to bubble acetylene through the hydridosilane. The acetylene flow rate was maintained at about 115 to 120 mL minute so as to yield approximately 120 to 170 g of vinylsilane product in a three to four hour run time. The gas exiting the SiH reservoir comprised acetylene and hydridosilane at a molar ratio within a range of 1.2:1 to 1.25:1. The gaseous mixture was passed into the stirring catalyst solution in the reactor. In those examples where a reaction occurred, an exotherm was evident within three minutes. The temperature of the reactor was controlled by means of a silicone oil bath to maintain the temperatures reported for each example. The exotherm usually peaked in 30 to 45 minutes. The reaction temperature was then maintained at a constant temperature as reported for each example for the remainder of the run. When the level of liquid in the reactor reached a preset mark on the flask corresponding to the approximate product weight as described in each example, the gas dispersion tube in the SiH reservoir was raised above the liquid level to stop any further hydrosilation. Acetylene flow was continued for an additional two to five minutes. The reactor was cooled to room temperature under nitrogen atmosphere and the product mixture was removed under nitrogen pressure into a preweighed bottle.

The weight of all products formed was obtained by subtracting the weight of the initial reaction mixture (i.e. catalyst, catalyst modifier, vinylsilane, and xylenes) from that of the final product mixture. Analysis of the mixture was performed by GC-TCD.

The catalysts used in the examples are as follows. A catalyst comprising a $Pt(COD)Cl_2$ complex was acquired from Strem Chemicals, Inc., Newbury, Mass.

The catalyst designated as "CPA/IPA/MeViSiCl$_2$" was prepared by the following method. A 500 mL, round-bottom flask, equipped with a stirring bar was flushed with nitrogen and charged with 296.2 g of distilled methylvinyldichlorosilane. 3.77 g of a solution comprising chloroplatinic acid in 1-propanol and containing 4.39 percent by weight platinum, obtained from Johnson-Matthey, Ward Hill, Mass., was slowly added to the flask. This mixture was stirred for about 15 hours under nitrogen and then transferred to a clean, stoppered glass bottle for storage.

The catalyst designated as "CPA/IPA/Me$_2$ViSiCl" was prepared by adding 2.51 g of the solution comprising chloroplatinic acid in 2-propanol, as described above, to 197.5 g of distilled Me$_2$ViSiCl. The resulting mixture was treated by a method similar to that described for preparing the CPA/IPA/MeViSiCl$_2$ catalyst.

In the examples the following labels apply. "Hydridosilane" describes the hydridosilane tested; "Catalyst" is the type of catalyst used, as previously described; "Catalyst Conc." is the initial g·atoms of platinum per mole of SiH added to the reactor; "COD" is the weight of 1,5-cyclooctadiene added to the reactor; "Additional MeViSiCl$_2$" and "Additional Me$_2$ViSiCl" is the weight of methylvinyldichlorosilane or dimethylvinylchlorosilane initially added to the reactor to vary the average concentration of vinylsilane in the reactor; "Xylenes" is the amount of a mixture of xylene isomers added to the reactor; "Temperature Range" describes the temperature range of the reactor that occurred from initiation of the exotherm to temperature stabilization; "Hold Temp." is the constant temperature the content of the reactor was held at after temperature stabilization. "Average MeViSiCl$_2$ Conc." and "Average Me$_2$ViSiCl Conc." is the average concentration by weight of these compounds in the reactor during a run; "Weight MeViSiCl$_2$" and "Weight Me$_2$ViSiCl" is the weight of methylvinyldichlorosilane or dimethylvinylchlorosilane made by the process, as determined by GC-TCD and corrected for any such compound initially added to the reactor; "Weight Bis-Silated Derivative" is the amount of the bis-silated acetylene made during conduct of the process; "P/B Weight Ratio" is the weight ratio of product MeViSiCl$_2$ or Me$_2$ViSiCl made during the run to bis-silated acetylene adduct; "Me" is methyl; and "Vi" is vinyl.

Example 1. (Reference example)

| | |
|---|---|
| Hydridosilane | MeHSiCl$_2$ |
| Catalyst | CPA/IPA/MeViSiCl$_2$ |
| Catalyst Conc. | 6 × 10$^{-5}$ g · atom Pt/mol SiH |
| COD | 0 g |
| Additional MeViSiCl$_2$ | 127 g |
| Xylenes | 148 g |
| Temperature Range | 67–79° C. |
| Hold Temperature | 77° C. |
| Average MeViSiCl$_2$ Conc. | 58 Wt. % |
| Weight Product MeViSiCl$_2$ | 165 g |
| Weight Bis-Silated Derivative | 11 g |
| P/B Weight Ratio | 15.4:1 |

Example 2.

| | |
|---|---|
| Hydridosilane | MeHSiCl$_2$ |
| Catalyst | Pt(COD)Cl$_2$ |
| Catalyst Conc. | 6 × 10$^{-5}$ g · atom Pt/mol SiH |
| COD | 0 g |
| Additional MeViSiCl$_2$ | 149 g |
| Xylenes | 148 g |
| Temperature Range | 72–82° C. |
| Hold Temperature | 76° C. |
| Average MeViSiCl$_2$ Conc. | 58 Wt. % |
| Weight Product MeViSiCl$_2$ | 164 g |
| Weight Bis-Silated Derivative | 8 g |
| P/B Weight Ratio | 21:1 |

Example 3. (Reference example)

| | |
|---|---|
| Hydridosilane | MeHSiCl$_2$ |
| Catalyst | Pt(COD)Cl$_2$ |
| Catalyst Conc. | 6 × 10$^{-5}$ g · atom Pt/mol SiH |
| COD | 0.013 g |
| Additional MeViSiCl$_2$ | 149 g |
| Xylenes | 149 g |

At the 3:1 mole COD to g·atom platinum ratio used in this example the reaction did not initiate at 70° C. and only a minor amount of methylvinyldichlorosilane was formed in the process.

Example 4. (Reference example)

| | |
|---|---|
| Hydridosilane | Me$_2$HSiCl |
| Catalyst | CPA/IPA/Me$_2$ViSiCl |
| Catalyst Conc. | 6 × 10$^{-5}$ g · atom Pt/mol SiH |
| COD | 0 g |
| Additional Me$_2$ViSiCl | 0 g |
| Xylenes | 275 g |
| Temperature Range | 56–69° C. |
| Hold Temperature | 63° C. |
| Average Me$_2$ViSiCl Conc. | 20 Wt. % |
| Weight Product Me$_2$ViSiCl | 118 g |
| Weight Bis-Silated Derivative | 6 g |
| P/B Weight Ratio | 19:1 |

Example 5.

| | |
|---|---|
| Hydridosilane | Me$_2$HSiCl |
| Catalyst | Pt(COD)Cl$_2$ |
| Catalyst Conc. | 6 × 10$^{-5}$ g · atom Pt/mol SiH |
| COD | 0 g |
| Additional Me$_2$ViSiCl | 22 g |
| Xylenes | 275 g |
| Temperature Range | 60–70° C. |
| Hold Temperature | 66° C. |
| Average Me$_2$ViSiCl Conc. | 21 Wt. % |
| Weight Product Me$_2$ViSiCl | 128 g |
| Weight Bis-Silated Derivative | 5 g |
| P/B Weight Ratio | 25.6:1 |

I claim:
1. A process for hydrosilation of an alkyne, the process comprising:

contacting at a temperature within a range of about 40° C. to 150° C. an alkyne described by formula $$R^1C\equiv CH,$$

where $R^1$ is selected from a group consisting of hydrogen atom and alkyls comprising one to about ten carbon atoms; with a hydridosilane described by formula $$(R^2)_nHSiX_{3-n},$$

where each $R^2$ is independently selected from a group consisting of alkyls comprising one to about 20 carbon atoms and aryls, each X is an independently selected halogen, and n=0 to 3; in the presence of a platinum catalyst consisting essentially of a cycloalkadiene-platinum complex described by formula PtR$^3_2$ or Pt(R$^3$)X$_2$, where R$^3$ is a cycloalkadiene comprising about six to 20 carbon atoms and X is as previously described.

2. A process according to claim 1 further comprising a non-complexed cycloalkadiene comprising about six to 20 carbon atoms, with the proviso that the ratio of moles of total cycloalkadiene to g·atom of platinum be less than about 5:1.

3. A process according to claim 1 further comprising a non-complexed cycloalkadiene comprising about six to 20 carbon atoms, with the proviso that the ratio of moles of total cycloalkadiene to g·atom of platinum be less than about 3:1.

4. A process according to claim 1 further comprising a non-complexed cycloalkadiene comprising about six to 20 carbon atoms, with the proviso that the ratio of moles of total cycloalkadiene to g·atom of platinum be less than about 2.5:1.

5. A process according to claim 1, where the contacting is effected at a pressure within a range of about 0.1 to 3 atmospheres.

6. A process according to claim 1, where the contacting is effected at a pressure within a range of about 1 to 3 atmospheres.

7. A process according to claim 1, where the contacting is conducted in a liquid phase using a liquid hydrocarbon solvent in which the alkyne and hydridosilane are soluble.

8. A process according to claim 1, where the contacting is effected at a temperature within a range of about 60° C. to 100° C.

9. A process according to claim 1, where the alkyne is acetylene, the hydridosilane is methyldichlorosilane, and the contacting is effected at a temperature within a range of about 70° C. to 80° C.

10. A process according to claim 1, where the alkyne is acetylene, the hydridosilane is dimethylchlorosilane, and the contacting is effected at a temperature within a range of about 60° C. to 70° C.

11. A process according to claim 1, where the alkyne is acetylene.

12. A process according to claim 1, where the hydridosilane is selected from a group consisting of methyldichlorosilane and dimethylchlorosilane.

13. A process according to claim 1, where the mole ratio of the alkyne to the hydridosilane is within a range of about 0.5:1 to 3:1.

14. A process according to claim 1, where the mole ratio of the alkyne to the hydridosilane is within a range of about 1:1 to 1.3:1.

15. A process according to claim 1, where the cycloalkadiene substituent of the platinum catalyst comprises about 6 to 10 carbon atoms.

16. A Process according to claim 1, where the cycloalkadiene substituent of the platinum catalyst is 1,5-cyclooctadiene.

17. A process according to claim 1, where the platinum catalyst is described by formula $Pt(R^3)Cl_2$ and $R^3$ is 1,5-cyclooctadiene.

18. A process according to claim 7, where the liquid phase comprises about 20 to 10,000 ppm platinum.

19. A process according to claim 18, where the alkyne is acetylene, the hydridosilane is methyldichlorosilane, the mole ratio of the alkyne to the hydridosilane is within a range of about 1:1 to 1.3:1, the platinum catalyst is described by formula $Pt(R^3)Cl_2$ and $R^3$ is 1,5-cyclooctadiene, and the contact is effected at a pressure within a range of about 1 to 3 atmospheres and a temperature within a range of about 70° C. to 80° C.

20. A process according to claim 18, where the alkyne is acetylene, the hydridosilane is dimethylchlorosilane, the mole ratio of the alkyne to the hydridosilane is within a range of about 1:1 to 1.3:1, the platinum catalyst is described by formula $Pt(R^3)Cl_2$ and $R^3$ is 1,5-cyclooctadiene, and the contact is effected at a pressure within a range of about 1 to 3 atmospheres and a temperature within a range of about 60° C. to 70° C.

* * * * *